United States Patent
Wang et al.

(10) Patent No.: US 11,976,090 B2
(45) Date of Patent: May 7, 2024

(54) D-PSICOSE CRYSTAL AND PREPARATION METHOD THEREOF

(71) Applicants: Sanying Wang, Luohe (CN); Linzheng Li, Luohe (CN); Ziheng Jin, Luohe (CN); Yanjun Wen, Luohe (CN)

(72) Inventors: Sanying Wang, Luohe (CN); Linzheng Li, Luohe (CN); Ziheng Jin, Luohe (CN); Yanjun Wen, Luohe (CN)

(73) Assignee: HENAN ZHONGDA HENGYUAN BIOTECHNOLOGY STOCK CO., LTD., Luohe (CN)

( * ) Notice: Subject to any disclaimer, the term of this patent is extended or adjusted under 35 U.S.C. 154(b) by 0 days.

(21) Appl. No.: 18/154,828

(22) Filed: Jan. 15, 2023

(65) Prior Publication Data
US 2023/0279037 A1   Sep. 7, 2023

(30) Foreign Application Priority Data
Mar. 4, 2022   (CN) .......................... 202210213217.5

(51) Int. Cl.
*C07H 1/06* (2006.01)
*C07H 3/02* (2006.01)

(52) U.S. Cl.
CPC .................. *C07H 1/06* (2013.01); *C07H 3/02* (2013.01)

(58) Field of Classification Search
CPC ..................................... C07H 1/06; C07H 3/02
See application file for complete search history.

(56) References Cited

U.S. PATENT DOCUMENTS

| 11,401,292 B2 * | 8/2022 | Kim | C07H 1/06 |
| 2011/0237790 A1 * | 9/2011 | Lee | C07H 1/06 536/127 |
| 2021/0171560 A1 * | 6/2021 | Nakagawa | C07H 1/06 |

FOREIGN PATENT DOCUMENTS

| CN | 114031649 A | * | 2/2022 | ............... C07H 1/06 |
| CN | 114031649 A | | 2/2022 | |
| WO | WO-2021239813 A1 * | | 12/2021 | ............... C07H 1/06 |
| WO | WO-2022117074 A1 * | | 6/2022 | ............... C07H 1/06 |

OTHER PUBLICATIONS

Zhao W, CN114031649A, Method for improving particle size and fluidity of psicose crystal, English Translation, Feb. 2022 (Year: 2022).*
Du Q, WO2022117074A1, Method for Preparing Crystalline D-Psicose, English Translation, Jun. 2022 (Year: 2022).*

* cited by examiner

*Primary Examiner* — Eric Olson
*Assistant Examiner* — Samuel L Galster

(57) ABSTRACT

The invention provides a D-psicose crystal and a preparation method thereof. The method comprises: adding a seed crystal to a D-psicose solution and stirring uniformly, subjecting the solution to crystallization by gradient cooling and constant-temperature crystallization alternately at 50-30° C., stopping the crystallization until the temperature of the solution is 30° C., separating the crystal by centrifugation, washing and drying, to obtain a D-psicose crystal. Rather than evaporative crystallization, organic solvent-assisted crystallization and ultrasonication, controllable crystallization by gradient cooling, constant-temperature crystallization, and other technical means are employed. Thus, the invention has low requirements for equipment, simple process, low energy consumption, and low preparation cost, and thus particularly suitable for large-scale industrial production and processing. The purity of the D-psicose crystal obtained is ≥98.5%, 80% by weight or more of the crystal has a grain size in the range of 20-40 meshes, and the yield per crystallization is ≥70%.

1 Claim, No Drawings

D-PSICOSE CRYSTAL AND PREPARATION METHOD THEREOF

This application claims priority to Chinese Patent Application No. 202210213217.5, filed on Mar. 4, 2022, which is incorporated by reference for all purposes as if fully set forth herein.

FIELD OF THE INVENTION

The present invention relates to the technical field of D-psicose preparation process, and particularly to a D-psicose crystal, and provides a preparation method of D-psicose crystal, which is suitable for use in industrial production.

DESCRIPTION OF THE RELATED ART

D-psicose is a hexose, a ketose, and an important rare sugar formed by the epimerization of D-fructose at the position C-3, which is mainly found in wheat, the plants of genus Itea, beet molasses, cane molasses and other materials in nature. Moreover, since fructose, when heated, is isomerized to produce D-psicose through non-enzymatic reactions, some foods that contain sugar and have been heat-treated also contain some D-psicose, such as baked goods, the sauce, steamed coffee, and juice treated at high temperature for a long period of time. D-psicose has a sweetness that is 70% of that of sucrose, but only 0.3% of the calories of sucrose, and similar taste and volume characteristics to those of sucrose. Unlike glucose, psicose is barely metabolized in the body after it's absorbed through the gut, so it doesn't produce energy, and hardly fermented and utilized by gut microbes, thus effectively reducing the energy intake. D-psicose also has the functions of regulating blood glucose, reducing fat and weight, preventing and treating type 2 diabetes mellitus and complications thereof. This characteristic of D-psicose is the most prominent advantage that allows it to act as an alternative sweetener. Moreover, D-psicose can undergo Maillard reactions with proteins or amino acids. Compared with other D-ketose (D-tagose, sorbose, and fructose, etc.), the reaction products have outstanding gellation properties, foamability, emulsifying stability and good oxidation resistance, and can improve the texture, flavor and taste of food.

At present, the methods for obtaining D-psicose crystal include organic solvent-assisted crystallization, evaporative crystallization, crystallization by supplementation of materials, and crystallization by repeatedly heating and cooling. The organic solvent-assisted crystallization requires organic solvents such as ethanol and acetone, and corresponding special equipment, which greatly increases the cost of production, and is not conducive to safe production. Since the concentration of D-psicose solution needs to be carried out at a lower temperature, evaporative crystallization requires a higher level of vacuum, and has high requirements for the equipment, which is not conducive to the production and operations. Crystallization by supplementation of materials facilitates the crystal growth; however, the production is cumbersome, the operability is poor, the yield is low, and the cost is high. Further, for crystallization by repeatedly heating and cooling, the grain size of the crystal obtained is small, and the yield is low.

Commercially available D-psicose products are mainly liquid products and powdered solid products. As a low-calorie sweetener, a powdered solid product of D-psicose tends to aggregate and is hard to dissolve quickly when added in a large amount, limiting the scope of application of the product. This problem can be well avoided by large grains of D-psicose crystal, and large grain also facilitates the separation of the crystal from the mother liquor. Few of the patented technologies that have been published so far can afford more large crystal grains. D-psicose crystal with large grains can be produced by the published evaporative crystallization, a higher level of vacuum is needed. In the cooling crystallization process, large grains can be obtained only with the aid of evaporative crystallization. Moreover, the grain is generally lower than that of the grain obtained by evaporative crystallization, and the yield is low. Moreover, the crystallization process also has an ultrasonication step in the process of crystallization by cooling. Although the crystal grain is increased, the operability is poor in the actual production process, the equipment cost is high, and it is difficult to achieve scale production.

SUMMARY OF THE INVENTION

The present invention aims to provide a method for preparing a D-psicose crystal, through a crystallization process comprising crystallization by gradient cooling and constant-temperature crystallization alternately. The present invention effectively solves the disadvantage of higher requirements for the equipment and production conditions existing in the prior art.

The crystallization method of the present invention is simple and efficient, the steps are simplified, the operability is high, the requirements on the equipment and production environment are low, the prepared crystal has a large grain size, and the yield is high, thus having significant economic benefits.

To achieve the above object, the present invention provides a method for preparing a D-psicose crystal. The method comprises specifically the following steps:

adding a seed crystal to a D-psicose solution, stirring until uniform, subjecting the resulting solution to crystallization by gradient cooling crystallization and constant-temperature crystallization alternately over a range of temperature from 50 to 30° C., stopping the crystallization until the temperature of the solution is 30° C., separating the crystal by centrifugation, washing with water, and drying, and to obtain a D-psicose crystal.

In a preferred embodiment, the D-psicose solution has a concentration in percent by weight of ≥83% (w/w), the purity of D-psicose is ≥95% (w/w), and the solution is maintained at a temperature of 50-60° C. Preferably, the D-psicose solution is obtained by catalyzing fructose by D-psicose-3 epimerase to obtain a mixed solution of D-psicose and fructose, followed by separation, purification, and concentration; and has a concentration of ≥83% (w/w) and the purity of D-psicose is ≥95% (w/w), on dry weight basis of D-psicose in the solution.

In a preferred embodiment, the seed crystal is D-psicose seed crystal, having a grain size ranging from 80 to 100 meshes, and added in an amount of 0.01-1% on dry weight basis of the D-psicose solution, preferably, in an amount of 0.02-0.7% on dry weight basis of the D-psicose solution, and more preferably, in an amount of 0.03%, 0.05%, 0.08%, 0.1%, 0.2%, 0.3%, 0.4%, 0.5%, and 0.6% on dry weight basis of the D-psicose solution.

In the crystallization process of the present invention, seed crystal having a grain size of 80-100 meshes is used and added in an amount that is suitably not too high. If the amount of the seed crystal added is too high, the seed crystal count is increased, affecting the final crystal grain size, having an adverse effect on the crystallization effect of the constant-temperature crystallization process, and resulting in a small crystal form. Therefore, the amount added is most preferably less than 0.1% on dry weight basis of the D-psicose solution.

In a preferred embodiment, the step of stirring until uniform comprises specifically: stirring for 20-30 s at a speed of 150-200 rpm after the seed crystal is added.

In the prior art, a grain growing step is generally added after the seed crystal is added. In order to skip this step, the present inventor finds through numerous experiments that the D-psicose crystal can be facilitate to grow slowly without the constant-temperature grain growing process, to effectively shorten the crystallization time, if the seed crystal is dispersed in the D-psicose by stirring at a high speed after addition and then cooled at a gradient of 0.02° C. to 0.2° C., where the temperature drop is controlled within a small range, the initial crystallization temperature is controlled at 50-60° C., the D-psicose solution is maintained to have a low supersaturation, and multiple constant-temperature crystallization process are combined.

In a preferred embodiment, the step of crystallization by gradient cooling comprises specifically: stirring the D-psicose solution added with the seed crystal at a temperature of 50° C., and undergoing gradient cooling at a rate of 0.02-0.2° C./h. Preferably, the cooling rate is 0.03-0.18° C./h, and the stirring rate is 10-100 rpm. More preferably, the cooling rate is 0.04, 0.05, 0.06, 0.07, 0.08, 0.09, 0.1, 0.12, 0.15, and 0.16° C./h, and the stirring rate is 20, 30, 40, 50, 60, 70, 80, and 90 rpm.

In the present invention, low supersaturation is maintained through a process of gradient cooling at a rate of 0.02-0.2° C., to reduce the probability of formation of small crystal nuclei and facilitate the growth of the crystal. The stirring at a speed of 10-100 rpm reduces the probability of the large crystal form being broken by the stirring rod. Further, the low stirring speed facilitates the crystallization of the D-psicose solution. However, if the crystallization process is not stirred, the crystallization speed will be greatly reduced, and the crystal form is inconsistent.

In a preferred embodiment, the step of constant-temperature crystallization comprises specifically: stirring the D-psicose solution for 8-15 h respectively at a constant temperature that is any temperature from the range of 47-45° C., the range of 43-42° C., the range of 41-40° C. and the range of 39-38° C. Preferably, the stirring at a constant temperature is continued for 8.0-15.0 h, and the stirring rate is 10-100 rpm. More preferably, the stirring at a constant temperature is continued for 12 h, and the stirring rate is 20, 30, 40, 50, 60, 70, 80, and 90 rpm.

In the present invention, each constant-temperature crystallization stage functions to perfect the crystal, to allow the crystal to have a generally uniform size, effectively increase the crystal grain size, alleviate the problem of formation of tiny crystals, and finally obtain a D-psicose crystal with large crystal form and centered crystal size distribution. The selection of the four temperature ranges in the present invention is made on the following basis: During the crystallization process, the gradient cooling in a low range in the early stage of crystallization ensures that the D-psicose solution is to have a low supersaturation, and constant-temperature crystallization in the above ranges of temperature allows the crystal to grow slowly, which avoids the generation of small crystal nuclei in the gradient cooling process to some extent. It is found through comparative tests that the effect of perfecting the crystal is more notable in the above four ranges, and the grain size and purity obtained by the crystallization process are better than those obtained in other temperature ranges.

In a preferred embodiment, the separation by centrifugation comprises centrifugation for 20-30 min at 4000-5000 rpm; and the drying comprises drying in a fluidized bed at 40-50° C. until the moisture content is less than 0.05%.

In a preferred embodiment, during the preparation process, the yield of D-psicose crystal per crystallization is ≥70%.

The present invention further aims to provide a D-psicose crystal prepared by the method as described above. The D-psicose crystal is detected to have a purity of ≥98.5%. 80 wt % of the crystal has a grain size ranging from 20-40 meshes.

Compared with related art, the D-psicose crystal and the preparation method thereof have the following advantages:

1. In the present invention, rather than evaporative crystallization, organic solvent-assisted crystallization and ultrasonication, controllable crystallization by gradient cooling, constant-temperature crystallization, and other technical means are employed. Thus, the present invention has low requirements for equipment, simple process, low energy consumption, and low preparation cost, thus being convenient for actual production, and particularly suitable for large-scale industrial production and processing. Moreover, crystal of high purity and large grain size can be obtained, thus solving the problem of limitation on the scope of application of the product, and having good application prospects.

2. In the present invention, the D-psicose crystal prepared by the simplified and optimized method has large grains, high purity, small grain size distribution, and other notable advantages, making the D-psicose product of large grains have a wide scope of applications and high cost advantage.

DETAILED DESCRIPTION OF THE PREFERRED EMBODIMENTS

Unless otherwise specified, the techniques used in the example are conventional techniques familiar to those skilled in the art, and the raw materials used are all commercially available products.

Unless otherwise indicated, Various raw materials, reagents, instruments and equipment used in the present invention are all commercially available or can be prepared by existing methods.

In the present invention, the crystallization apparatus, stirrer, fluidized bed and drying device are all devices available to technicians in the art, as long as they can meet the specified conditions, and there is no need to change or adjust the devices.

In the present invention, the yield is calculated by the formula: Yield (%)=(weight of dried D-psicose crystal/weight of D-psicose in D-psicose solution before crystallization)×100%.

In the present invention, the rate of crystal grain size distribution is calculated by the mass fraction of the crystal, that is, the percentage of the crystal mass within a certain size range relative to the total crystal mass.

Example 1

A method for preparing D-psicose crystal comprises specifically the following steps:

D-psicose seed crystal was added to a D-psicose solution, where the D-psicose solution had a concentration of 83 wt %, the purity of D-psicose was 98.0%, the grain size of the D-psicose seed crystal was 80 meshes, and the D-psicose seed crystal was added in an amount of 0.1% on dry weight basis of the D-psicose solution. After the seed crystal was added, the solution was stirred at 150 rpm for 20 s.

The temperature of the D-psicose solution was lowered from 50° C. to 45.2° C. at a rate of 0.2° C./h, followed by constant-temperature crystallization for 11 h at 45.2° C.

After constant-temperature crystallization at 45.2° C., the temperature was lowered to 42° C. at a rate of 0.2° C./h, followed by constant-temperature crystallization for 12 h at 42° C.

After constant-temperature crystallization at 42° C., the temperature was lowered to 40.6° C. at a rate of 0.2° C./h, followed by constant-temperature crystallization for 12 h at 40.6° C.

After constant-temperature crystallization at 40.6° C., the temperature was lowered to 38.4° C. at a rate of 0.2° C./h, followed by constant-temperature crystallization for 12 h at 38.4° C.

After constant-temperature crystallization at 38.4° C., the temperature was lowered to 30° C. at a rate of 0.2° C./h, and then the crystallization was stopped. The stirring speed was controlled at 50 rpm during the whole crystallization process.

After crystallization, the solution was centrifuged at 4000 rpm for 20 min. The crystal was collected, washed 2-3 times with pure water, and dried in a fluidized bed at 45° C. to a moisture content of less than 0.05%. The crystal was sieved, and the purity of the product was detected by HPLC. A D-psicose product with a purity of 99.8% (w/w) and 82% of the grains having a size ranging from 20-40 meshes was obtained, and the yield of the crystallization process was 72%. Detailed grain size distribution rates are shown in Table 1.

TABLE 1

| Grain size | Distribution rate (%) |
| --- | --- |
| Less than 20 meshes | 3.86 |
| 20-40 meshes | 82 |
| 40-60 meshes | 8.21 |
| Greater than 60 meshes | 5.93 |

Example 2

A method for preparing D-psicose crystal comprises specifically the following steps:

D-psicose seed crystal was added to a D-psicose solution, where the D-psicose solution had a concentration of 84 wt %, the purity of D-psicose was 98.0%, the grain size of the D-psicose seed crystal was 100 meshes, and the D-psicose seed crystal was added in an amount of 0.3% on dry weight basis of the D-psicose solution. After the seed crystal was added, the solution was stirred at 150 rpm for 20 s.

The temperature of the D-psicose solution was lowered from 50° C. to 45.9° C. at a rate of 0.1° C./h, followed by constant-temperature crystallization for 12 h at 45.9° C.

After constant-temperature crystallization at 45.9° C., the temperature was lowered to 42° C. at a rate of 0.2° C./h, followed by constant-temperature crystallization for 12 h at 42° C.

After constant-temperature crystallization at 42° C., the temperature was lowered to 40.6° C. at a rate of 0.2° C./h, followed by constant-temperature crystallization for 12 h at 40.6° C.

After constant-temperature crystallization at 40.6° C., the temperature was lowered to 38.4° C. at a rate of 0.2° C./h, followed by constant-temperature crystallization for 12 h at 38.4° C.

After constant-temperature crystallization at 38.4° C., the temperature was lowered to 30° C. at a rate of 0.2° C./h, and then the crystallization was stopped. The stirring speed was controlled at 50 rpm during the whole crystallization process.

After crystallization, the solution was centrifuged at 4000 rpm for 20 min. The crystal was collected, washed 2-3 times with pure water, and dried in a fluidized bed at 45° C. to a moisture content of less than 0.05%. The crystal was sieved, and the purity of the product was detected by HPLC. A D-psicose product with a purity of 99.4% (w/w) and 80.5% of the grains having a size ranging from 20-40 meshes was obtained, and the yield of the crystallization was 71.2%. Detailed grain size distribution rates are shown in Table 2.

TABLE 2

| Grain size | Distribution rate (%) |
| --- | --- |
| Less than 20 meshes | 3.45 |
| 20-40 meshes | 80.5 |
| 40-60 meshes | 8.2 |
| Greater than 60 meshes | 7.85 |

Example 3

A method for preparing D-psicose crystal comprises specifically the following steps:

D-psicose seed crystal was added to a D-psicose solution, where the D-psicose solution had a concentration of 84 wt %, the purity of D-psicose was 98.0%, the grain size of the D-psicose seed crystal was 80 meshes, and the D-psicose seed crystal was added in an amount of 0.1% on dry weight basis of the D-psicose solution. After the seed crystal was added, the solution was stirred at 150 rpm for 20 s.

The temperature of the D-psicose solution was lowered from 50° C. to 45.2° C. at a rate of 0.2° C./h followed by constant-temperature crystallization for 11 h at 45.2° C.

After constant-temperature crystallization at 45.2° C., the temperature was lowered to 42.4° C. at a rate of 0.2° C./h, followed by constant-temperature crystallization for 10 h at 42.4° C.

After constant-temperature crystallization at 42.4° C., the temperature was lowered to 40.6° C. at a rate of 0.2° C./h, followed by constant-temperature crystallization for 12 h at 40.6° C.

After constant-temperature crystallization at 40.6° C., the temperature was lowered to 38.4° C. at a rate of 0.2° C./h, followed by constant-temperature crystallization for 12 h at 38.4° C.

After constant-temperature crystallization at 38.4° C., the temperature was lowered to 30° C. at a rate of 0.2° C./h, and then the crystallization was stopped. The stirring speed was controlled at 50 rpm during the whole crystallization process.

After crystallization, the solution was centrifuged at 4000 rpm for 20 min. The crystal was collected, washed 2-3 times with pure water, and dried in a fluidized bed at 45° C. to a moisture content of less than 0.05%. The crystal was sieved, and the purity of the product was detected by HPLC. A D-psicose product with a purity of 99.6% (w/w) and 81.3% of the grains having a size ranging from 20-40 meshes was obtained, and the yield of the crystallization was 70.9%. Detailed grain size distribution rates are shown in Table 3.

TABLE 3

| Grain size | Distribution rate (%) |
| --- | --- |
| Less than 20 meshes | 3.82 |
| 20-40 meshes | 81.3 |
| 40-60 meshes | 8.03 |
| Greater than 60 meshes | 6.85 |

Example 4

A method for preparing D-psicose crystal comprises specifically the following steps:

D-psicose seed crystal was added to a D-psicose solution, where the D-psicose solution had a concentration of 84 wt %, the purity of D-psicose was 98.0%, the grain size of the D-psicose seed crystal was 80 meshes, and the D-psicose seed crystal was added in an amount of 0.1% on dry weight basis of the D-psicose solution. After the seed crystal was added, the solution was stirred at 150 rpm for 20 s.

The temperature of the D-psicose solution was lowered from 50° C. to 45.2° C. at a rate of 0.2° C./h, followed by constant-temperature crystallization for 11 h at 45.2° C.

After constant-temperature crystallization at 45.2° C., the temperature was lowered to 42° C. at a rate of 0.2° C./h, followed by constant-temperature crystallization for 12 h at 42° C.

After constant-temperature crystallization at 42° C., the temperature was lowered to 40.2° C. at a rate of 0.2° C./h, followed by constant-temperature crystallization for 12 h at 40.2° C.

After constant-temperature crystallization at 40.2° C., the temperature was lowered to 38.4° C. at a rate of 0.2° C./h, followed by constant-temperature crystallization for 12 h at 38.4° C.

After constant-temperature crystallization at 38.4° C., the temperature was lowered to 30° C. at a rate of 0.2° C./h, and then the crystallization was stopped. The stirring speed was controlled at 50 rpm during the whole process.

After crystallization, the solution was centrifuged at 4000 rpm for 20 min. The crystal was collected, washed 2-3 times with pure water, and dried in a fluidized bed at 45° C. to a moisture content of less than 0.05%. The crystal was sieved, and the purity of the product was detected by HPLC. A D-psicose product with a purity of 99.8% (w/w) and 80.6% of the grains having a size ranging from 20-40 meshes was obtained, and the yield of the crystallization was 71%. Detailed grain size distribution rates are shown in Table 4.

TABLE 4

| Grain size | Distribution rate (%) |
| --- | --- |
| Less than 20 meshes | 3.03 |
| 20-40 meshes | 80.6 |
| 40-60 meshes | 8.72 |
| Greater than 60 meshes | 7.65 |

Example 5

A method for preparing D-psicose crystal comprises specifically the following steps:

D-psicose seed crystal was added to a D-psicose solution, where the D-psicose solution had a concentration of 84 wt %, the purity of D-psicose was 98.0%, the grain size of the D-psicose seed crystal was 80 meshes, and the D-psicose seed crystal was added in an amount of 0.1% on dry weight basis of the D-psicose solution. After the seed crystal was added, the solution was stirred at 150 rpm for 20 s.

The temperature of the D-psicose solution was lowered from 50° C. to 45.2° C. at a rate of 0.2° C./h, followed by constant-temperature crystallization for 11 h at 45.2° C.

After constant-temperature crystallization at 45.2° C., the temperature was lowered to 42° C. at a rate of 0.2° C./h, followed by constant-temperature crystallization for 12 h at 42° C.

After constant-temperature crystallization at 42° C., the temperature was lowered to 40.6° C. at a rate of 0.2° C./h, followed by constant-temperature crystallization for 12 h at 40.6° C.

After constant-temperature crystallization at 40.6° C., the temperature was lowered to 38.8° C. at a rate of 0.2° C./h, followed by constant-temperature crystallization for 12 h at 38.8° C.

After constant-temperature crystallization at 38.8° C., the temperature was lowered to 30° C. at a rate of 0.2° C./h, and then the crystallization was stopped. The stirring speed was controlled at 50 rpm during the whole process.

After crystallization, the solution was centrifuged at 4000 rpm for 20 min. The crystal was collected, washed 2-3 times with pure water, and dried in a fluidized bed at 45° C. to a moisture content of less than 0.05%. The crystal was sieved, and the purity of the product was detected by HPLC. A D-psicose product with a purity of 99.5% (w/w) and 80.9% of the grains having a size ranging from 20-40 meshes was obtained, and the yield of the crystallization was 71.5%. Detailed grain size distribution rates are shown in Table 5.

TABLE 5

| Grain size | Distribution rate (%) |
| --- | --- |
| Less than 20 meshes | 3.43 |
| 20-40 meshes | 80.9 |
| 40-60 meshes | 8.02 |
| Greater than 60 meshes | 7.65 |

Example 6

A method for preparing D-psicose crystal comprises specifically the following steps:

D-psicose seed crystal was added to a D-psicose solution, where the D-psicose solution had a concentration of 83 wt %, the purity of D-psicose was 98.0%, the grain size of the D-psicose seed crystal was 80 meshes, and the D-psicose seed crystal was added in an amount of 0.08% on dry weight basis of the D-psicose solution. After the seed crystal was added, the solution was stirred at 150 rpm for 20 s.

The temperature of the D-psicose solution was lowered from 50° C. to 45.2° C. at a rate of 0.2° C./h, followed by constant-temperature crystallization for 11 h at 45.2° C.

After constant-temperature crystallization at 45.2° C., the temperature was lowered to 42° C. at a rate of 0.2° C./h, followed by constant-temperature crystallization for 12 h at 42° C.

After constant-temperature crystallization at 42° C., the temperature was lowered to 40.6° C. at a rate of 0.2° C./h, followed by constant-temperature crystallization for 12 h at 40.6° C.

After constant-temperature crystallization at 40.6° C., the temperature was lowered to 38.4° C. at a rate of 0.2° C./h, followed by constant-temperature crystallization for 12 h at 38.4° C.

After constant-temperature crystallization at 38.4° C., the temperature was lowered to 30° C. at a rate of 0.2° C./h, and then the crystallization was stopped. The stirring speed was controlled at 50 rpm during the whole crystallization process.

After crystallization, the solution was centrifuged at 4000 rpm for 20 min. The crystal was collected, washed 2-3 times with pure water, and dried in a fluidized bed at 45° C. to a moisture content of less than 0.05%. The crystal was sieved, and the purity of the product was detected by HPLC. A D-psicose product with a purity of 99.6% (w/w) and 81.2% of the grains having a size ranging from 20-40 meshes was obtained, and the yield of the crystallization was 71.4%. Detailed grain size distribution rates are shown in Table 6.

TABLE 6

| Grain size | Distribution rate (%) |
| --- | --- |
| Less than 20 meshes | 3.36 |
| 20-40 meshes | 81.2 |
| 40-60 meshes | 8.01 |
| Greater than 60 meshes | 7.43 |

Comparative Example 1 a D-psicose crystal was prepared according to the method described in Example 1, except that the constant-temperature crystallization for 11 h at 45.2° C., constant-temperature crystallization for 12 h at 42° C., constant-temperature crystallization for 12 h at 40.6° C. and constant-temperature crystallization for 12 h at 38.4° C. were omitted. That is, the D-psicose solution was cooled from 50° C., at a rate of 0.2° C./hr, and then the crystallization was stopped after the temperature was lowered to 30° C. The other steps were the same as those in Example 1. A D-psicose product with a purity of 99.3% (w/w) and 20.4% of the grains having a size ranging from 20-40 meshes was obtained, and the yield of the crystallization was 72%. Detailed grain size distribution rates are shown in Table 7.

TABLE 7

| Grain size | Distribution rate (%) |
| --- | --- |
| Less than 20 meshes | 1.21 |
| 20-40 meshes | 20.4 |
| 40-60 meshes | 42.65 |
| Greater than 60 meshes | 35.74 |

Comparative Example 2 a D-psicose crystal was prepared according to the method described in Example 1, except that the grain size of the Dpsicose seed crystal added was 60 meshes. The other steps were the same as those in Example 1. A D-psicose product with a purity of 98.7% (w/w) and 40.2% of the grains having a size ranging from 20-40 meshes was obtained, and the yield of the crystallization was 68.9%. Detailed grain size distribution rates are shown in Table 8.

TABLE 8

| Grain size | Distribution rate (%) |
| --- | --- |
| Less than 20 meshes | 1.33 |
| 20-40 meshes | 40.2 |
| 40-60 meshes | 38.4 |
| Greater than 60 meshes | 20.07 |

Comparative Example 3 a D-psicose crystal was prepared according to the method described in Example 1, except that the grain size of the Dpsicose seed crystal added was 150 meshes. The other steps were the same as those in Example 1. A D-psicose product with a purity of 98.4% (w/w) and 38.5% of the grains having a size ranging from 20-40 meshes was obtained, and the yield of the crystallization was 71.2%. Detailed grain size distribution rates are shown in Table 9.

TABLE 9

| Grain size | Distribution rate (%) |
| --- | --- |
| Less than 20 meshes | 1.14 |
| 20-40 meshes | 38.5 |
| 40-60 meshes | 39.8 |
| Greater than 60 meshes | 20.56 |

Comparative Example 4 a D-psicose crystal was prepared according to the method described in Example 1, except that the stirring speed was controlled at 150 rpm during the whole crystallization process. The other steps were the same as those in Example 1. A D-psicose product with a purity of 99.2% (w/w) and 36.7% of the grains having a size ranging from 20-40 meshes was obtained, and the yield of the crystallization was 70.8%. Detailed grain size distribution rates are shown in Table 10.

TABLE 10

| Grain size | Distribution rate (%) |
| --- | --- |
| Less than 20 meshes | 1.02 |
| 20-40 meshes | 36.7 |
| 40-60 meshes | 37.9 |
| Greater than 60 meshes | 24.38 |

The foregoing descriptions of specific exemplary embodiments of the present invention are illustrative and exemplary, and these descriptions are not intended to limit the present invention to specific forms disclosed. Obviously, various changes and variations can be made according to the above teachings. The choice and description of exemplary embodiments are intended to explain the specific principles and practical applications of the present invention, so that the technicians in the art can realize and utilize various exemplary embodiments of the present invention as well as various options and changes. The scope of the present invention is intended to be limited by the claims and their equivalents.

What is claimed is:

1. A method for preparing a D-psicose crystal, comprising:

adding a seed crystal to a D-psicose solution and stirring uniformly, wherein the D-psicose solution has a concentration in percent by weight of ≥83% w/w, a purity of D-psicose is ≥95% w/w, and the D-psicose solution is maintained at a temperature of 50-60° C.; the seed crystal is a D-psicose seed crystal, having a grain size ranging from 80 to 100 meshes, and being added in an amount of 0.01-1% on dry weight basis of the D-psicose solution; and the D-psicose solution is stirred for 20 seconds at a speed of 150 rpm after the seed crystal is added, subjecting the D-psicose solution to crystallization by a gradient cooling crystallization and a constant-temperature crystallization alternately over a range of temperature from 50 to 30° C., wherein the gradient cooling crystallization comprises: stirring the D-psicose solution with the seed crystal at a temperature of 50° C., with gradient cooling at a rate of 0.02-0.2° C./h; and the constant-temperature crystallization comprises: stirring the D-psicose solution for 8-15 hours at a constant temperature that is any temperature from the range of 47-45° C., the range of 43-42° C., the range of 41-40° C. and the range of 39-38° C., stopping the crystallization until the temperature of the D-psicose solution is 30° C., separating a crystal by centrifugation, wherein the separation by centrifugation comprises centrifugation for 20-30 min at 4000-5000 rpm; and during preparation process, a yield of the D-psicose crystal per crystallization is ≥70%, washing the crystal with water, and drying to obtain the D-psicose crystal, wherein the drying comprises: drying in a fluidized bed at 40-50° C. until a moisture content is less than 0.05%, wherein a distribution rate of the D-psicose crystal having a grain size of 20-40 meshes is 80.5% to 82.0%.

* * * * *